US006962695B1

(12) United States Patent
Berglund (10) Patent No.: US 6,962,695 B1
(45) Date of Patent: Nov. 8, 2005

(54) MODIFICATION OF INTERFERON ALPHA PRODUCTION

(75) Inventor: Åsa Berglund, Umeå (SE)

(73) Assignee: Bionative AB, Umeå (SE)

( * ) Notice: Subject to any disclaimer, the term of this patent is extended or adjusted under 35 U.S.C. 154(b) by 0 days.

(21) Appl. No.: 09/869,269

(22) PCT Filed: Dec. 22, 1999

(86) PCT No.: PCT/SE99/02446

§ 371 (c)(1),
(2), (4) Date: Jul. 11, 2001

(87) PCT Pub. No.: WO00/39163

PCT Pub. Date: Jul. 6, 2000

(30) Foreign Application Priority Data

Dec. 29, 1998 (SE) .................................... 9804583

(51) Int. Cl.[7] ........................ A61K 38/21; C12N 21/04; C07K 14/56

(52) U.S. Cl. ................... 424/85.7; 424/85.4; 424/93.1; 424/93.21; 424/93.6; 424/93.71; 435/70.1; 435/70.3; 435/325; 530/351

(58) Field of Search ............................... 435/325, 70.1, 435/70.3; 530/351; 424/93.1, 85.4, 85.7, 424/93.21, 93.6, 93.71

(56) References Cited

U.S. PATENT DOCUMENTS

| | | | |
|---|---|---|---|
| 3,932,617 A | 1/1976 | Nichol, Jr. et al. | |
| 4,027,021 A | 5/1977 | Underwood | |
| 4,266,024 A | 5/1981 | Swetly et al. | |
| 4,780,413 A * | 10/1988 | Johnston | ..................... 435/70.2 |

FOREIGN PATENT DOCUMENTS

| | | |
|---|---|---|
| EP | 0 000 520 B1 | 2/1979 |
| EP | 0 048 283 A1 | 3/1982 |
| EP | 0 097 353 A2 | 1/1984 |

OTHER PUBLICATIONS

Fan et al., "Increased Efficacy of Human Natural Interferon α (IFN-αn3) Versus Human Recombinant IFN-α2 for Inhibition of HIV-1 Replication in Primary Human Monocytes", AIDS Research and Human Retroviruses, 1993, 1115-1123, 9(11), Mary Ann Liebert, Inc., Publishers, Larchmont, NY, USA.

Heim et al., "Cultured Human Myocardial Fibroblasts of Pediatric Origin: Natural Human Interferon-α is More Effective than Recombinant Interferon-α 2a in Carrier-state Coxsackievirus B3 Replication", J. Mol. Cell Cardiol, 1995, 2119-2208, 27, Academic Press Limited, Burlington, MA, USA.

Weissmann et al., "Structure and Expression of Human IFN-α Genes", Phil. Trans. R. Soc. Lond., 1982, 7-82, 299, The Royal Society, London, United Kingdom.

Antonelli et al., "Interferon Antibodies in Patients with Infectious Diseases", Biotherapy, 1997, 7-14, 10, Kluwer Academic Publishers, The Netherlands.

Öberg et al., "The Incidence and Clinical Significance of Antibodies to Interferon-α in Patients with Solid Tumors", Biotherapy, 1997, 1-5, 10, Kluwer Academic Publishers, The Netherlands.

Goren et al., "Human Monocytes and Lymphocytes Produce Different Mixtures of α-Interferon Subtypes", 1986, 323-329, 6, Mary Ann Liebert, Inc., Publishers, Larchmont, NY, USA.

Gabrilovac et al., "Leu-enkephalin Enhances Interferon Secretion in Mice", Res Exp Med, 1996, 137-144, 196, Experimental Medicine, Springer-Verlag, The Netherlands.

Mezentseva et al., The Influence of Ridostin and Cycloferonum on IFN Production in Cells of MIce with T- and B-Immunodeficites, Gamaleya Institute of Epidemiology and Microbiology, Moscow, Russia.

Galabov et al., "Dipyridamole Induces Interferon in Man", Biomedicine & Pharmacotherapy, 1984, 412-413, 38, Elsevier Science, New York, NY, USA.

Stringfellow et al., "Interferon induction by 5-Halo-6-Phenyl Pyrimidinones", Journal of Interferon Research, 1980, 1-14, 1(1), Mary Ann Liebert, Inc., Publishers, Larchmont, NY, USA.

Chelbi-Alix et al., "Ethanol Induces 2',5'-Oligoadenylate Synthetase and Antiviral Activities through Interferon-β Production", The Journal of Biological Chemistry, 1992, 1741-1745, 267(3), The American Society for Biochemistry and Molecular Biology, Inc., USA.

(Continued)

Primary Examiner—Janet Andres
Assistant Examiner—Jegatheesan Seharaseyon
(74) Attorney, Agent, or Firm—Burns, Doane, Swecker & Mathis, LLP (57) ABSTRACT

A process for the production of α-interferon comprising the steps: i) inducing of human leukocytes by means of a virus; ii) treating the leukocytes with an enhancing agent selected from: a) Xanthine, pyrimidinol and pyrimidinone or derivatives of anyone thereof, such as theophylline, 2-amino-5-bromo-6-methyl-4 pyriminidol or thymine; b) an organic solvent selected from the group consisting of non-aromatic ketones, aliphatic or cyclic amides, alkylated aliphatic or cyclic urea derivatives and aliphatic or cyclic sulfoxides, such as N-methyl-2-pyrrolidinone, acetone, 2-butanone, 1,3-dimethyl-2-imidazolidinone, dimethylsulfoxide, 4-methyl-2-pentanone-N-ethyl-2-pyrrolidinone, 2-pyrrolidinone, tetramethylene sulfoxide or N,N-dimethylacetamide; or a combination of the compounds from a) with an organic solvent from b).

15 Claims, 5 Drawing Sheets

OTHER PUBLICATIONS

Lin et al., Role of Calmodulin/Protein Kinase C in Interferon Production by Poly(rl)—Poly(rC) in Primed Human Cell Cultures, Journal of Interferon Research, 1990, 375-378, 10, Mary Ann Liebert, Inc., Publishers, Larchmont, NY, USA.

Zahorska et al., "Influence of Theophylline on Interferon Production and cAMP Level in Lpa Cells", Archivum Immunologiae et Therapiae Experimentalis, 1995, 43-46, 43, Polish Academy of Sciences, Wroclaw, Poland.

Sandberg et al., "A Distinct Population of Nonphagocytic and Low Level $CD4^+$ Null Lymphocytes Produce IFN-α after Stimulation by Herpes Simplex Virus-Infected Cells", The Journal of Immunology, 1990, 1015-1020, 145, The American Association of Immunologist, USA.

Cantell et al., "Production of Interferon in Human Leukocytes from Normal Donors with the Use of Sendai Virus", Methods in Enzymology, 1981, 29-38, 78, Academic Press, Inc., Burlington, MA, USA.

Morser et al., "Low Temperature Treatment of Namalwa Cells Causes Superproduction of Interferon", J. Gen. Virol., 1981, 163-174, 56, Society for General Microbiology, Reading, United Kingdom.

E. Slattery et al. "Mouse Interferon: Production by Ehrlich Ascites Tumour Cells Infected with Newcastle Disease Virus and its Enhancement by Theophylline"*J. Gen. Virol* (1980) 49: 91-96.

Annekatrin Stecher et al., "Interferon-α Yields From Sendai Virus-Induced Human Leukocyte Cultures Are Enhanced by Lowering the Incubation Temperature", J. gen. Virol, (1984), pp. 635 to 638, vol. 65, Printed in Great Britain.

Haye et al., ATCC Cell Lines and Hybridomas, $8^{th}$ Edition, 1994, cover page and p. 45, The American Type Culture Collection, Rockville, MD.

Namalwa, DSMZ No. ACC 24, DSMZ-Deutsche Sammlung von Milroorganismen und Zellkulturen GmbH, Germany.

Sell et al, Immunology, Immunopathology & Immunity, $5^{th}$ Edition, cover page, Figure 2-8, pp. 42 and 827, Appleton & Lange, Stamford, CT.

Lackie et al., The Dictionary of Cell Biology, $2^{nd}$ Edition, cover page, pp. 364 and 292, Academic Press, Boston, MA.

Freshney, Culture of Animal Cells, A Manual of Basic Technique, $4^{th}$ Edition, pp. 5-6, 16-17, 259-260, 269 and 273, A John Wiley & Sons, Inc., New York, NY.

* cited by examiner

MODIFICATION OF INTERFERON ALPHA PRODUCTION

FIELD OF INVENTION

The present invention is directed to a process for the production of α-interferon in human leukocytes induced by virus. More particularly the invention relates to a process of production of α-interferon in which process the leukocytes are treated with an enhancing agent.

BACKGROUND OF THE INVENTION

The Interferons constitutes a family of proteins characterized by their non-specific antiviral and antiproliferative activity, a property that has made them useful as antiviral and anticancer drugs. Interferons are produced and released by animal cells upon exposure to a variety of inducing agents, the most potent of which are viruses. They are classified into three types: α-Interferon, β-Interferon, and γ-Interferon, based on serological and structural relations. The use of interferons as therapeutic drugs dates back to the 1970's. Although all three types of interferons have been subject to evaluation, α-interferon has become most widely used for therapeutic purposes. Among the interferons of human origin, the α-interferons are divided into several subtypes, which are either encoded by different gene loci or alleles of those, while there is only one subtype each of human β- and γ-interferon. The function of each subtype is still not clear, and the molecular or cellular targets of their antiviral and antineoplastic activities is thus not fully investigated. However, some in vitro studies have shown a larger biological effect when a mixture of different subtypes was used compared to using a single subtype only (Fan, S. X, Skillman, D. R, Liao, M-J, Testa, D. and Meltzer, M. S. (1993) *AIDS Res. And Human Retrovir.* 9, 1115–1122, Heim, A., Brehm, C., Stille-Siegener, M., Müller, G., Hake, S, Kandolf, R. and Figulla, H-R. (1995) *J. Mol. Cell Cardiol.* 27, 2199–2208).

There are presently three major methods for industry-scale production of α-interferon, all with fundamental differences in the cell system used. In the procaryotic systems, the gene coding for a single subtype, almost exclusively interferon α2, has been transferred to *Escherichia coli*, whereby this protein is expressed by the bacteria and subsequently harvested (Wessmann, C., Hagata, S., Boll, W., et al (1982) *Phil. Trans. Royal Soc. London, Series B: Biol. Sci.* 299 7–28). This process for the production of α-interferon is referred to herein as "recombinant interferon". The bacterial cultures can be used for producing α-interferon at high efficiency, leading to an economically advantageous alternative to cells of human origin. However, only one single subtype is produced and the proteins are not modified (e.g. glycosylated) in contrast to interferon α2 that is produced in eukaryotic cells. A clinical drawback encountered with the recombinant α-interferon products is their tendency to induce antibodies against α-interferon in some patients. These neutralising antibodies have in several publications been shown to negatively affect the therapeutic treatment with recombinant α-interferon (Antonelli, G., Simeoni, E., Currenti, M., DePisa, F., Colizzi, V., Pistello, M., and Dianzani, F., (1997) Biother 10, 7–14, Öberg, K. and Alm, G. (1997) *Biother* 10, 1–5).

Alternatively α-interferon can be produced in human cells, either from established cell lines which are grown in vitro, or from primary cells, e.g., from peripheral leukocytes obtained as by-products from donated blood. In these case a mixture of α-interferon subtypes is obtained, although different cell sources produce a different subtype pattern. (Goren, T., Fischer, D. G. and Rubinstein M. (1986) *J. Interferon Res.* 6, 323–329. Established cell lines are clones derived from human tumors or from cells that have been immortalised, e.g., by the treatment with Epstein-Barr virus. These cells divide and grow indefinitely, in suitable media and under appropriate conditions. In contrast, interferon-producing primary cells such as leukocytes do not divide and have a finite life span. Such cells are consequently in limited supply, and their availability is a limiting factor for large scale production of native leukocyte α-interferon. Means for increasing the yield in the production process are therefore necessary.

Eucaryotic cell systems produce very little or no α-interferon spontaneously. The use of an "inducer" is therefore needed to initiate the production of α-interferon by the cells. Consequently, a large number of factors have been reported to initiate the production of α-interferon in various in vitro cell systems or in vivo. The most common inducers are different viruses, but synthetic organic substances have also been shown to act as inducers for the production of α-interferon. Some examples are leu-enkephalin and naloxone in vivo in mice (Gabrilovac, J., Ikic-Sutlic, M., Knezevic, N. and Poljak, L. (1996) *Res. Exp. Med.* 196, 137–144), neovir in vivo in mice (Mezentseva M., Narovlyansky, A., Kondratieva, T and Ershov, F. (1997). *J. Interferon Res.* 17, Suppl. 2, S94. Abstract), dipyridamole in vivo in humans (Galabov A. S. and Mastikova M. (1984) *Biomed. Pharmacoth.* 38, 412–413), 2-amino-5-bromo-6-methyl-4-pyrimidinol (2-ABMP) and its derivatives in vivo in humans (U.S. Pat. No. 3,932,617, Stringfellow, D. A., Vanderberg, H. C. and Weed, S. D. (1980) *J. Interferon Res.* 1, 1–14) and antraquinone derivatives in vivo in a variety of species (U.S. Pat. No. 4,027,021). Ethanol is reported to induce β-interferon production in Madin-Darby bovine kidney (MDBK) cells in the absence of other inducers (Chelbi-Alix, M. K. and Chousterman, S. (1992) *J. Biol. Chem.* 267, 1741–1745).

There are some examples where the production of α-interferon has been increased by ancillary reagents, termed herein as "enhancers", i.e., compound(s) which is/are capable of increasing the production of α-interferon in cells activated by an inducing agent, but does not itself induce production of a α-interferon. Characteristic of an enhancer is that it can be added either before the agent that induces α-interferon, or after the induction has taken place. Substances that are reported as enhancers of interferon production in human cells are, e.g., the calmodulin inhibitor trifluoperazine used on fibroblasts (Lin, H-Y. and Thacore, H. R. (1990) *J. Interferon Res.* 10, 375–378), dexamethasone used as a stimulator on a cell line of lymphoblastoid origin (U.S. Pat. No. 4,266,024) and sodium butyrate, also used as a stimulant in a lymphoblastoid cell line (EP 0097 353, EP 0000520). Furthermore, it has been reported that the purine derivative theophylline acts as an enhancer and increases the yield of α-interferon from mouse Lpa cells induced by poly I:C (Zahorska, R., Korbecki, M., and Barciszewski, J. (1995) *Arch. Immunol. Ther. Exp.* 43, 43–46), and the use of some synthetic organic compounds, preferably tetramethylurea (TMU) (European Patent No 0 097 353), or dimethylsulfoxide (DMSO) (U.S. Pat. No. 4,266,024) has been shown to increase the α-interferon yield from a lymphoblastoid cell line treated with an inducer.

In the work leading to the present invention some of the substances which has been reported as inducers or enhancers when used in vivo or on fibroblasts and on a cell line of lymphoblastoid origin has been tested on human leukocytes, with the aim to increase the α-interferon production, both before or after induction with Sendai virus, but without any positive result on the yield of α-interferon. In some experiments even a decrease in α-interferon production from human leukocytes was observed when adding compounds known as enhancers in cell lines. For instance, pre-treatment with sodium butyrate has been described as a stimulant that leads to an increased yield of α-interferon in a lymphoblastoid cell line (European Patent No 0 097 353; European Patent No 0 000 520). In the present work it was found that pre-treatment of primary leukocytes with sodium butyrate according to a similar procedure led to a decrease in the yield of α-interferons, which points at fundamental differences between cell lines and primary cells as production systems for α-interferon proteins.

It is accordingly an object of the present invention to provide an improved process for production of α-interferon in human leukocytes induced by virus.

SUMMARY OF THE INVENTION

The object of the invention is obtained by the process for the production of α-interferon as claimed in the claims.

According to the invention there is provided a process for the production of α-interferon comprising the steps:
i) inducing of human leukocytes by means of a virus,
ii) treating the leukocytes with an enhancing agent selected from
a) Xanthine, pyrimidinol and pyrimidinone or derivatives of anyone thereof;
b) an organic solvent selected from the group consisting of non-aromatic ketones, aliphatic or cyclic amides, alkylated aliphatic or cyclic urea derivatives and aliphatic or cyclic sulfoxides; or a combination of the compounds from a) with an organic solvent from b).

According to the present invention, it was surprisingly found that the addition of the compounds and/or an organic solvent as indicated above, increases the amount of virus induced α-interferon in leukocytes. Considering the different species in the case of the mouse Lpa cells and the different cell source in the case of the lymphoblastoid cell line, and considering the lack of consistency between the different cell systems in the experiments described above, it was surprisingly found that theophylline as well as a solvent such as dimethylsulfoxide enhanced the production of α-interferon in virus induced primary leukocytes. Also, the pyrimidine derivative 2-amino-5-bromo-6-methyl-4-pyrimidinol (2-ABMP), was found to act as an enhancing agent of the α-interferon production according to the present invention using virus induced primary leukocytes. Since 2-ABMP did not induce α-interferon in the absence of a viral inducer using the experimental system described in this invention, the mechanism for enhancement is obviously different for the in vivo α-interferon induction described in the literature, as compared to the α-interferon production enhancing effect of this substance observed in the present invention. This further strengthens the evidence that different mechanisms are in effect in different human cell systems, and indicates the unpredictiveness in working with additives to cellular systems or organisms.

As mentioned above several agents have been used as inducers and enhancers in both in vivo systems and in different cell culture systems. Since the data in the literature in many cases deviated from the findings in the present invention e.g. the inability for 2-ABMP to act as an interferon inducer in the cell system according to the invention, several unique properties of the cellular system in this invention should be pointed out. Primary cells from peripheral blood represent a resting cell population in contrast to all the other cellular systems described for interferon production. The cells are not activated or immortalised by virus, as is the case for Burkitt's lymphoma cells or so called lyphoblastoid cells. Nor are they tumor cell lines with their inherent genomic instability and dysregulated gene expression. It has been shown that within a mixture of leukocytes derived from human blood the monocytes are the main producers of α-interferon after Sendai virus treatment (Sandberg, K., Matsson, P. And Alm, G. (1990) *J. Immunology* 145, 1015–1020). Thus, the cells used in this invention differ from the established cell lines used for α-interferon production with respect to growth state, neoplastic potential, presence of viral genome and cell type. The effects of the tested factors are therefore a priori not expected to be the same as for other cell types, with differences in differentiation, metabolic state or interference from viral genomes.

DETAILED DESCRIPTION OF THE INVENTION

According to the present invention it was found that addition of enhancing agents in the form of xanthine, pyrimidinol and pyrimidinone or derivatives of anyone thereof and/or various organic solvents significantly increases the interferon production in human leukocytes induced by virus. The enhancing agent can increase the interferon yield either alone or in a combination of an organic solvent and the mentioned compounds. At certain conditions the effect of combining these enhancing agents is synergistic, showing a larger effect than the one obtained using the substances separately.

The xanthine derivatives that can be used according to the invention are xanthine with aliphatic and/or aromatic substituens, such as theophylline, theobromine, enprophylline, hypoxanthine and 8-phenyltheophylline. Theophylline is a preferred enhancing agent. Pyrimidinol derivatives that can be used are for example 2-amino-5-bromo-6-methyl-pyrimidinol and 2-amino-6-methyl-4-pyrimidinol with 2-amino-5-bromo-6-methyl-pyrimidinol as a preferred embodiment. A preferred pyrimidinone derivative is thymine.

The organic solvents that can be used according to the invention are non-aromatic ketones, aliphatic or cyclic amides, alkylated aliphatic or cyclic urea derivatives and aliphatic or cyclic sulfoxides. As preferred solvents can be mentioned acetone, 2-butanone, 1,3-dimethyl-2-imidazolidinone, dimethylsulfoxide, N-ethyl-2-pyrrolidinone, 4-methyl-2-pentanone, N-methyl-2-pyrrolidinone (NMP), 2-pyrrolidinone, tetramethylene sulfoxide, N,N-dimethylacetamide, 2-pyrrolidinone. The most preferred compounds presented under item a) above with respect to interferon production is theophylline and 2-ABMP. The most preferred solvent is NMP.

The virus used can be any virus, but the preferred virus is Sendai virus, the most potent inducer of interferon-α for purified human leukocytes.

Leukocyte purification, incubation of the cells and induction by virus are mainly performed according to the original method of Cantell et al. (Cantell, K., Hirvonen, S., Kauppinen, H-L. and Myllylä, G. (1981) Methods in Enzymology 78, 29–38).

The human leukocytes used according to the invention are prepared from buffy coats by an initial centrifugation to fractionate the components, followed by sequential removal of the plasma layer and of the leukocyte fraction by suction. Residual red blood cells contaminating the leukocyte fraction are lysed twice with 2–4 volumes of cold 0.83% ammonium chloride and each lysis step is followed by centrifugation to collect the cells. The final leukocyte fraction is resuspended in a basal medium, e.g. EMEM (Eagle's minimum essential medium) supplemented with polyethylene glycol-(PEG)-precipitated human plasma. PEG-precipitated plasma is prepared by adding PEG 6000 to a final concentration of 6% (w/w) to human plasma. After precipitation for 3–5 days in a cold room the supernatant is removed and stored frozen until used. The temperature of the incubation medium is set to 36–37° C. and continuous stirring is used. Human PEG-precipitated plasma is added to a concentration of 1–5% (v/v), preferably 4% (v/v). A low amount of α-interferon (normally 100 IU/ml) is added to the incubation medium as a priming step, but other concentrations, up to several thousands of units per ml can be used. Human leukocytes are then added to a concentration of about 3–15 million cells per mL, preferably 7–11 million cells per mL. The similar size of the enhancing effect observed using the different cell concentrations makes it probable that the effect can be seen also at cell concentrations outside this range. The priming step is normally allowed to proceed for 1–5 hours, preferably 1.5–2 hours.

Induction of interferon is performed by addition of Sendai virus, generally 30 mL virus from allantoic fluid per liter incubation medium but both smaller and larger amounts showed good inducing capacity and the most preferred range is 500–2000 hemagglutinating virus particles per cell. A decrease of the incubation temperature to 29° C. –32° C. is performed (Morser, J. And Shuttleworth, J. (1981) *J. Gen. Virology* 56, 163–174) after another 1 to 4 hours, preferable after 1 to 2 hours.

The optimal timing for adding the different enhancing agents varies, but in general an increase in α-interferon production is seen when the substances are added either at the same time as the cells or up to several hours after the induction, preferentially close to the time of the temperature decrease.

The concentration range where the additives are effective in increasing the interferon production varies between the different compounds but for the least toxic solvents a positive effect can be seen in the range of 1 mM–0.3 M, preferably in the range of 3 mM–50 mM and most preferably within 5 mM–20 mM. For the more toxic solvents the suitable concentration lies within the more limited ranges. For the theophylline, 2-amino-5-bromo-6-methyl-4-pyrimidinol and thymine the effective range is 5 $\mu$M–0.5 mM, preferably 20 $\mu$M–0.15 mM. After these additions, the incubation is allowed to proceed overnight with continuous stirring. A centrifugation step is performed to remove the cells and the supernatants are analysed by an ELISA to quantify α-interferon.

The invention will now be illustrated with the following non-limiting examples and with reference to the figures:

Figure Legends

FIG. 1A

Effect on α-interferon production in Sendai virus induced human leukocytes by addition of different organic solvents to the incubation medium. The amount of α-interferon produced is calculated as percent of a reference with no addition of organic solvents (=100%).

FIG. 1B

Effect on α-interferon production in Sendai virus induced human leukocytes by addition of different organic solvents in combination with 2-ABMP to the incubation medium. The amount of α-interferon produced is calculated as percent of a reference with no addition of enhancing agent (=100%).

FIG. 2

Effect on α-interferon production in Sendai virus induced human leukocytes by addition of different purine and pyrimidine derivatives at different NMP concentrations. The amount of α-interferon produced is calculated as percent of a reference with no addition of enhancing agents (=100%).

FIG. 3

Effect on α-interferon production in Sendai virus induced human leukocytes by addition of different amounts of theophylline at different DMSO concentrations. The amount of α-interferon produced is calculated as percent of a reference with no addition of enhancing agents (=100%).

FIG. 4

Effect on α-interferon production in Sendai virus induced human leukocytes by addition of NMP and theophylline to the incubation medium in laboratory scale fermentors. The amount of α-interferon produced is calculated as percent of a reference with no addition of enhancing agents (=100%).

Table 1

Effect on α-interferon production of addition of enhancing agents, 2-ABMP and DMSO, both to Sendai virus induced human leukocytes and to non induced human leukocytes.

EXAMPLE 1

α-Interferon Production by Sendai Virus Induced Human Leukocytes after Incubation with Various Organic Solvents.

Human leukocytes prepared from buffy coats and used in concentrations between 8 and 11 million cells per mL are incubated in a basal media (either EMEM or a modified EMEM) supplemented with 1.5 g/L of tricine and 4% (v/v) PEG precipitated plasma. The experiments are performed in a volume of 40 mL medium in 100 mL glass bottles under continuous stirring. The cells are primed with 100 IU/mL α-interferon for 1.5 hours at 37° C. before addition of 30 mL/L Sendai virus. After 1.5 hours the incubation temperature is decreased to 30° C. and the organic solvents are added to the incubation medium. The solvent used are acetone, DMSO (final concentration: 5 mL/L), 2-butanone, NN-dimethylacetamide, NMP, tetramethylene sulfoxide (2.5 mL/L), TMU (1.5 mL/L), 2-pyrrolidinone (1.25 mL/L), 4-metyl-2-pentanone, 1,3-dimetyl-2-imidazolidinone and N-ethyl-2-pyrrolidinone (0.6 mL/L). The incubation is then allowed to proceed overnight. The cells are removed by a centrifugation step and the supernatants are analysed by an ELISA to quantify α-interferon.

Figure 1A:
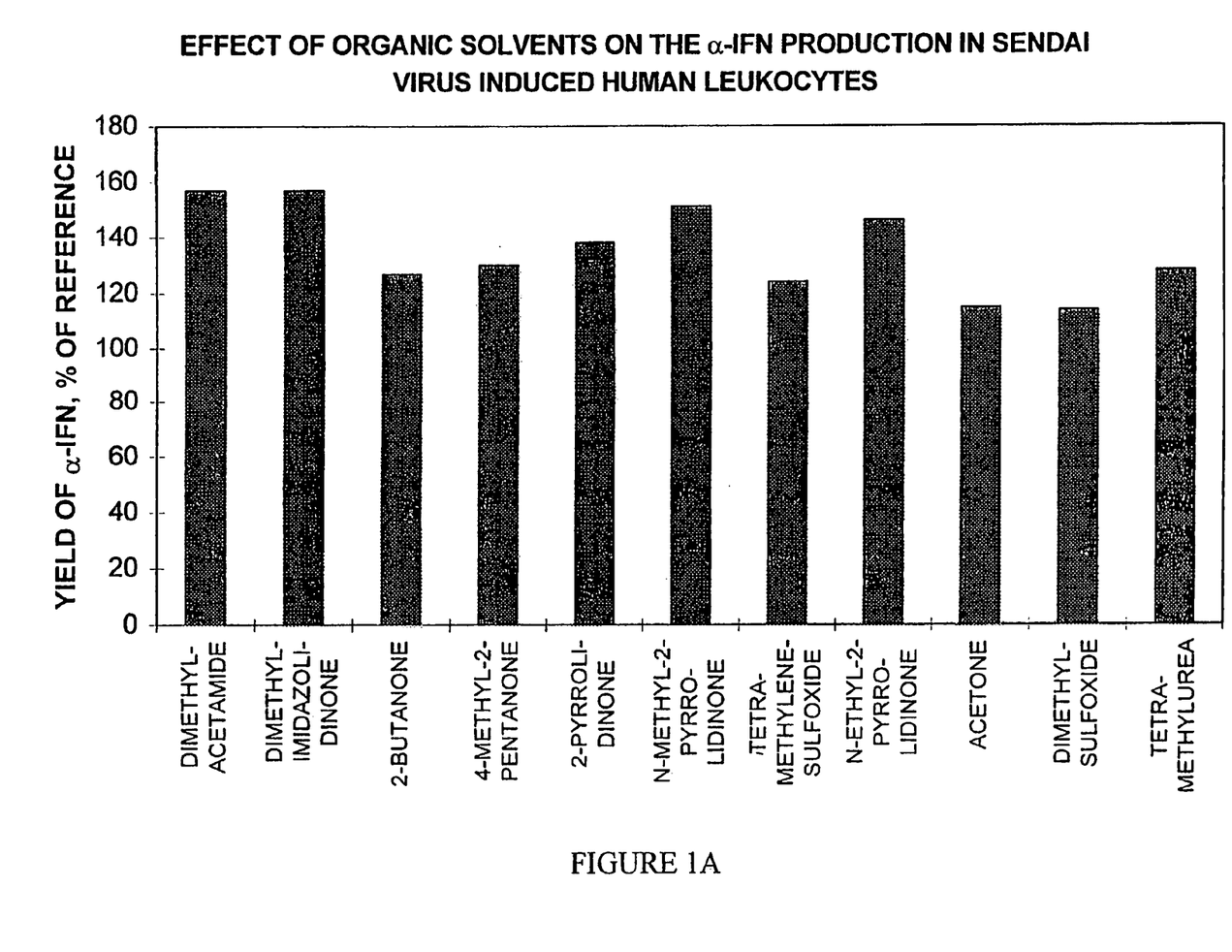

The results are shown in FIG. 1A.

Figure 1B:
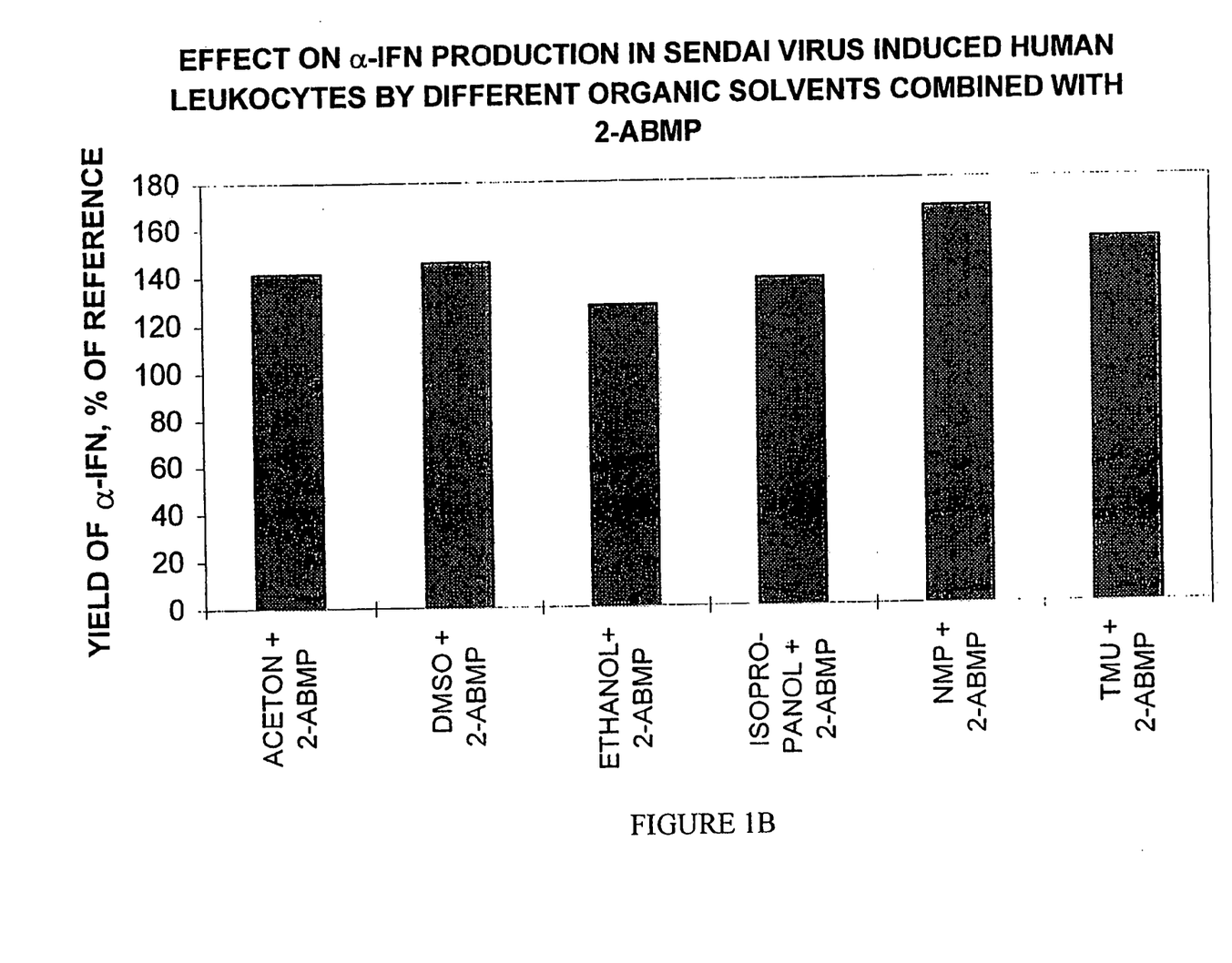

The above incubation conditions are used for the example shown in FIG. 1B, but in this case some of the organic solvents are combined with 50 to 100 $\mu$g/mL of 2-ABMP.

EXAMPLE 2

α-Interferon Production in Sendai Virus Induced Human Leukocytes after Incubation with Purine and Pyrimidine Derivatives, in the Absence or Presence of an Organic Solvent.

Example 1 is repeated with the same incubation conditions but with addition of one purine and two pyrimidine derivatives either alone or in combination with NMP. The purine used is theophylline (50 μg/ml) and the pyrimidines are 2-ABMP (50 μg/ml) or thymine (140 μg/ml).

Figure 2:
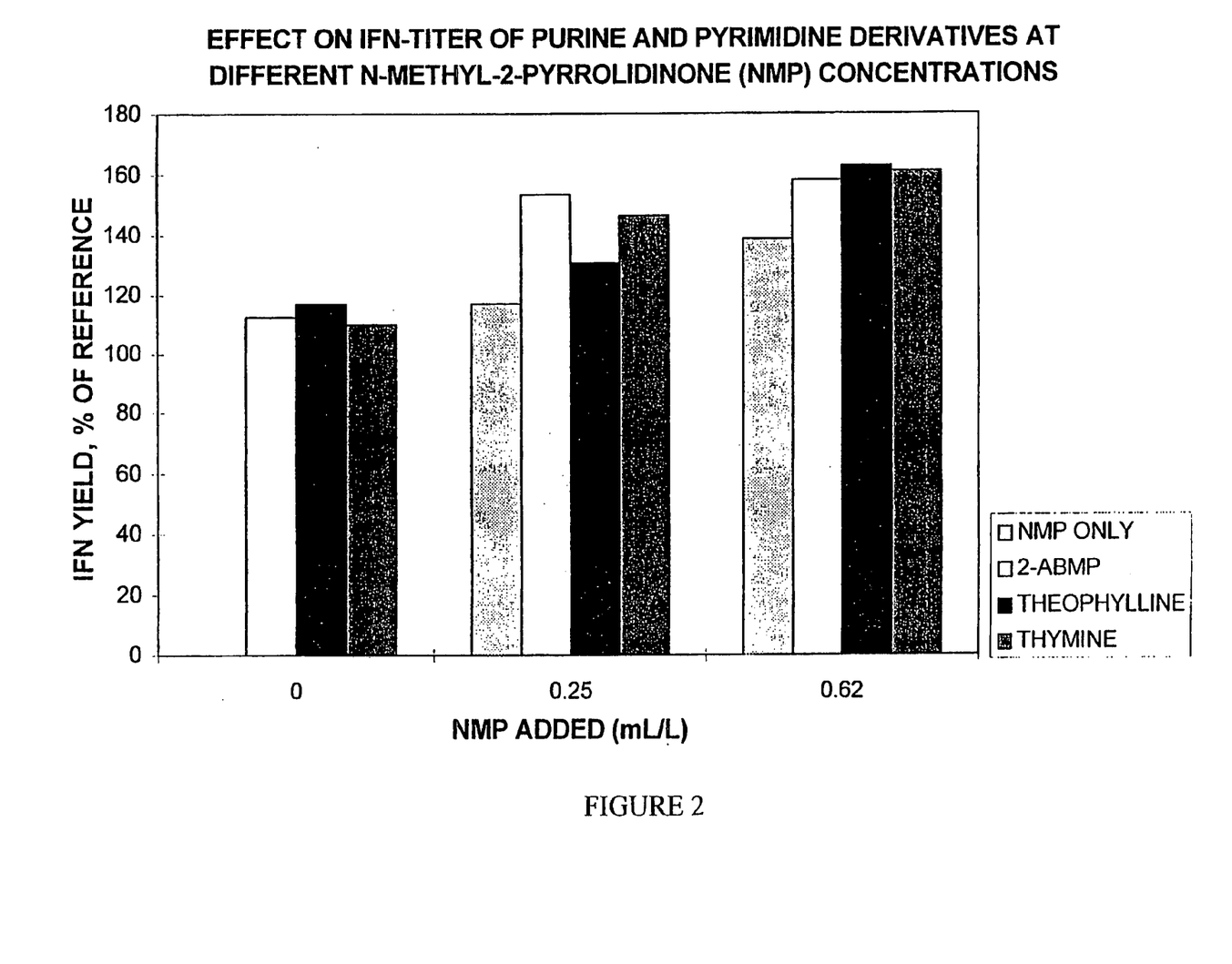

The results are shown in FIG. 2.

EXAMPLE 3

α-Interferon Production in SENDAI Virus Induced Human Leukocytes after Incubation with Theophylline and an Organic Solvent at Varying Concentrations.

The procedure from example 1 is repeated but with addition of the organic solvent DMSO and the purine theophylline. DMSO is added at 2.5 mL/L or 5 mL/L. The theophylline concentration varies between 5 μg/mL to 100 μg/mL.

Figure 3:
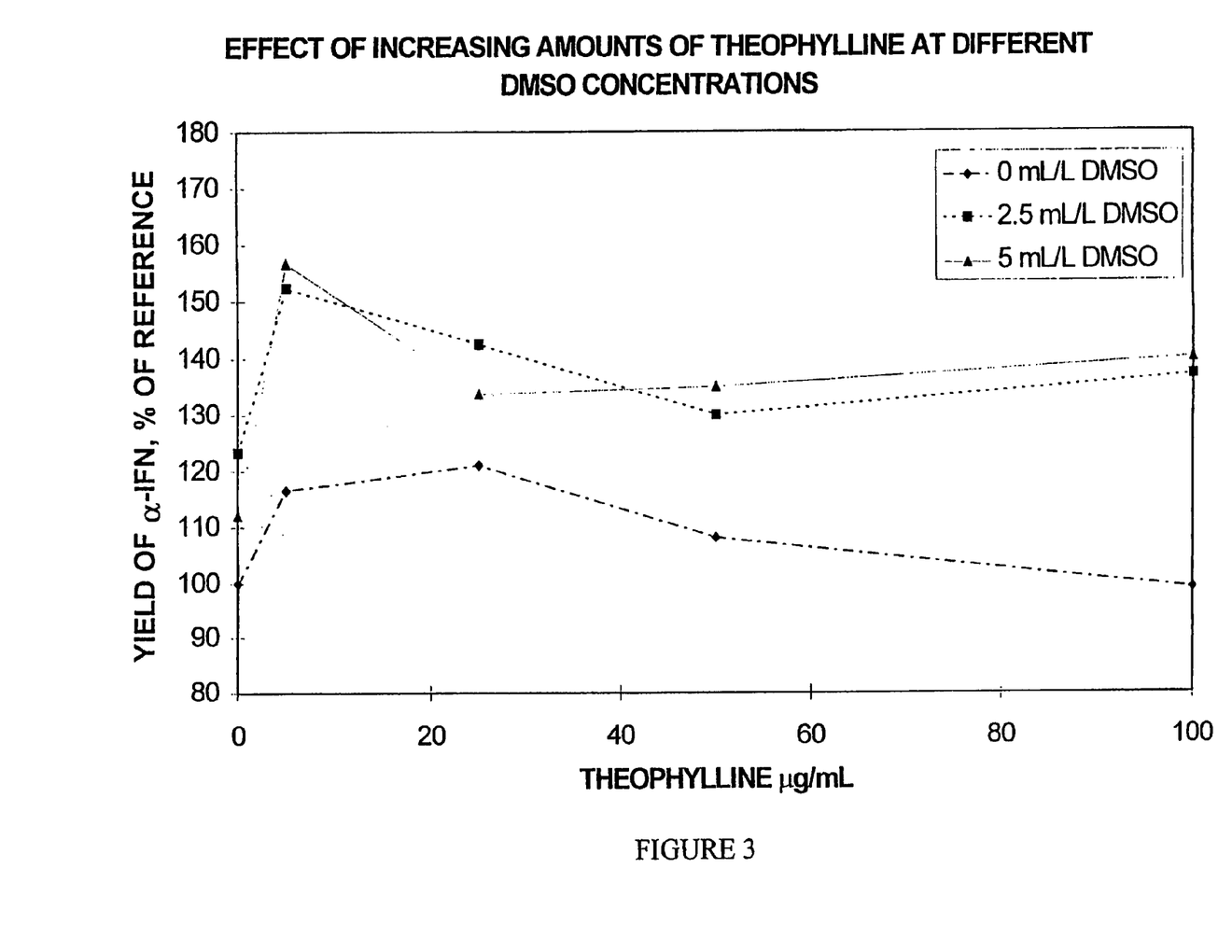

The results are shown in FIG. 3.

Figure 4:
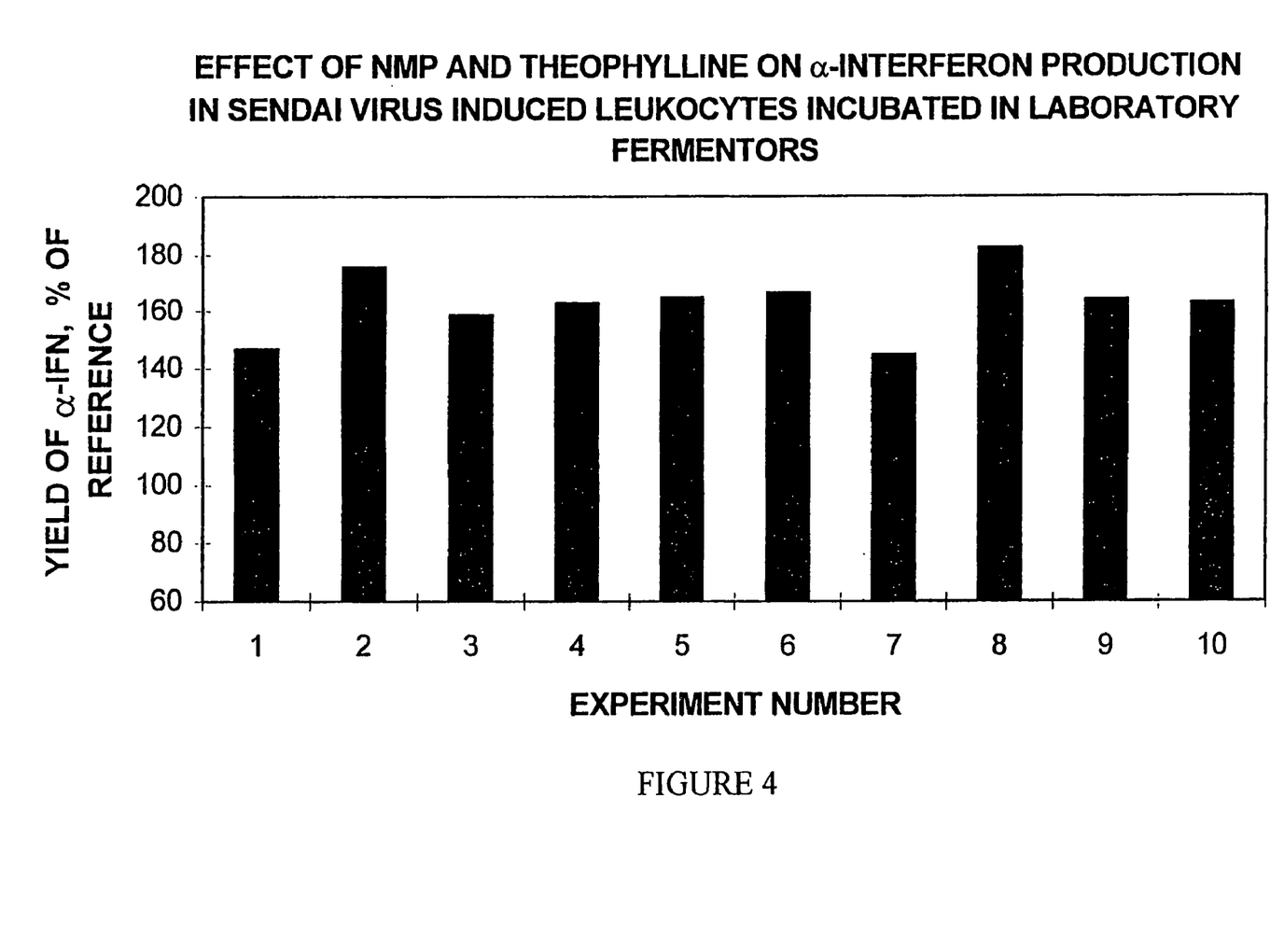

EXAMPLE 4

α-Interferon Production in Sendai Virus Induced Human Leukocytes Incubated in Laboratory Scale Fermentors An up-scaling is performed where the results obtained in the small scale is used to find suitable conditions for the laboratory fermentors. Different experiments are made to compare the α-interferon production in a fermentor where NMP and theophylline are added with a reference fermentor where no enhancing agent is added. The experiments are performed in laboratory scale fermentors using 2 L medium per vessel. The amount of theophylline is 50 μg/mL, while NMP varies from 1.75 mL/L to 3 mL/L. The incubation conditions are in accordance with Example 1. The results are shown in FIG. 4.

EXAMPLE 5

α-interferon production in human leukocytes incubated with 2-ABMP and DMSO. Effects of virus induction.

Example 1 is repeated with the same incubation conditions but with addition of 2-ABMP in combination with DMSO. The enhancing agents are added both to Sendai virus induced leukocytes and to non induced leukocytes and the effect on the α-interferon production is compared. The 2-ABMP is added at a concentration of 50 μg/ml and the amount of DMSO added is 5 mL/L.

The results are shown in Table 1.

TABLE 1

| Viral induction | Enhancing agent | Yield of α-interferon |
|---|---|---|
| Sendai virus (30 mL/L) | None | 100% |
| Sendai virus (30 mL/L) | 2-ABMP (50 μg/mL) and DMSO (5 mL/L) | 146% |
| None | 2-ABMP (50 μg/mL) and DMSO (5 mL/L) | <1% |

CONCLUSION

In the present invention it has been shown that addition of different organic solvents as well as different purines and pyrimidines reproducibly increases the production of α-interferon in virus induced human leukocytes. The largest increase is obtained when the purine or pyrimidine derivatives are combined with an organic solvent.

What is claimed is:

1. A process for the production of α-interferon comprising the steps:
   i) inducing of human leukocytes by means of a virus,
   ii) treating the leukocytes with an enhancing agent selected from
      a) xanthine, pyrimidinol and pyrimidinone, theophylline, theobromine, enprophylline, hypoxanthine, 8-phenyltheophylline, 2-amino-5-bromo-6-methylpyrimidinol, 2-amino-6-methyl-4-pyrimidinol and thymine;
      b) an organic solvent selected from the group consisting of non-aromatic ketones, aliphatic or cyclic amides, alkylated aliphatic or cyclic urea derivatives and aliphatic or cyclic sulfoxides; or a combination of the compounds from a) with an organic solvent from b).

2. A process according to claim 1, characterized in that the virus is Sendai virus.

3. A process according to claim 2, characterized in that the enhancing agent is theophylline.

4. A process according to claim 1, characterized in that the enhancing agent is theophylline.

5. A process according to claim 1, characterized in that the organic solvent is any of acetone, 2-butanone, 1,3-dimethyl-2-imidazolidinone, dimethylsulfoxide, N-ethyl-2-pyrrolidinone, 4-methyl-2-pentanone, N-methyl-2-pyrrolidinone, 2-pyrrolidinone, tetramethylene sulfoxide or N,N-dimethylacetamide.

6. A process according to claim 5, characterized in that the solvent is N-methyl-2-pyrrolidinone.

7. A process according to claim 1, characterized in that the enhancing agent is added at the same time or up to 4 hours after the virus induction.

8. A process according to claim 7, characterized in that the virus is Sendai virus.

9. A process according to claim 7, characterized in that the enhancing agent is theophylline.

10. A process according to claim 1, characterized in that the leukocytes are monocytes.

11. A process according to claim 10, characterized in that the enhancing agent is added at the same time or up to 4 hours after the virus induction.

12. A process according to claim 11, characterized in that the virus is Sendai virus.

13. A process according to claim 10, characterized in that the virus is Sendai virus.

14. A process according to claim 10, characterized in that the enhancing agent is theophylline.

15. A process according to claim 10, characterized in that the organic solvent is any of acetone, 2-butanone, 1,3-dimethyl-2-imidazolidinone, dimethylsulfoxide, N-ethyl-2-pyrrolidinone, 4-methyl-2-pentanone, N-methyl-2-pyrrolidinone, 2-pyrrolidinone, tetramethylene sulfoxide or N,N-dimethylacetamide.

* * * * *